(12) United States Patent
Srinivasan et al.

(10) Patent No.: US 7,524,457 B2
(45) Date of Patent: Apr. 28, 2009

(54) DISPLACEMENT CHEMICAL REGENERATION METHOD AND APPARATUS

(75) Inventors: Kannan Srinivasan, Sunnyvale, CA (US); Christopher A. Pohl, Union City, CA (US)

(73) Assignee: Dionex Corporation, Sunnyvale, CA (US)

( * ) Notice: Subject to any disclaimer, the term of this patent is extended or adjusted under 35 U.S.C. 154(b) by 550 days.

(21) Appl. No.: 10/179,725

(22) Filed: Jun. 24, 2002

(65) Prior Publication Data
US 2002/0197727 A1    Dec. 26, 2002

Related U.S. Application Data

(62) Division of application No. 09/520,731, filed on Mar. 8, 2000, now Pat. No. 6,436,719.

(51) Int. Cl.
*G01N 30/02* (2006.01)
*G01N 30/26* (2006.01)

(52) U.S. Cl. .............. 422/70; 436/161; 210/198.2; 73/61.56

(58) Field of Classification Search .............. 436/161; 422/70; 210/635, 638, 656, 659, 662, 663, 210/198.2, 677; 73/61.56
See application file for complete search history.

(56) References Cited

U.S. PATENT DOCUMENTS

| | | | |
|---|---|---|---|
| 4,171,757 A | 10/1979 | Diamond | 222/389 |
| 4,242,097 A | 12/1980 | Rich, Jr. et al. | |
| 4,455,233 A | 6/1984 | Pohl et al. | |
| 4,999,098 A | 3/1991 | Pohl et al. | 204/301 |
| 5,248,426 A | 9/1993 | Stillian et al. | 210/635 |
| 5,352,360 A | 10/1994 | Stillian et al. | 210/198.2 |
| 5,567,307 A | 10/1996 | Karmarkar | |
| 5,597,734 A | 1/1997 | Small et al. | 436/161 |
| 5,633,171 A | 5/1997 | Small et al. | 436/161 |
| 5,773,615 A | 6/1998 | Small et al. | 436/161 |

FOREIGN PATENT DOCUMENTS

| | | |
|---|---|---|
| WO | 94/18555 | 8/1994 |
| WO | 99/44054 | 9/1999 |
| WO | 01/67091 | 9/2001 |

*Primary Examiner*—Jan M Ludlow
(74) *Attorney, Agent, or Firm*—Morgan, Lewis & Bockius LLP; David J. Brezner

(57) ABSTRACT

Apparatus for chromatographically separating ionic species in an aqueous electrolyte-containing eluent to form an effluent, suppressing the effluent, detecting the suppressed effluent and passing the detected effluent to a regenerant reservoir, thereby displacing the regenerant to flow to the suppressor.

4 Claims, 4 Drawing Sheets

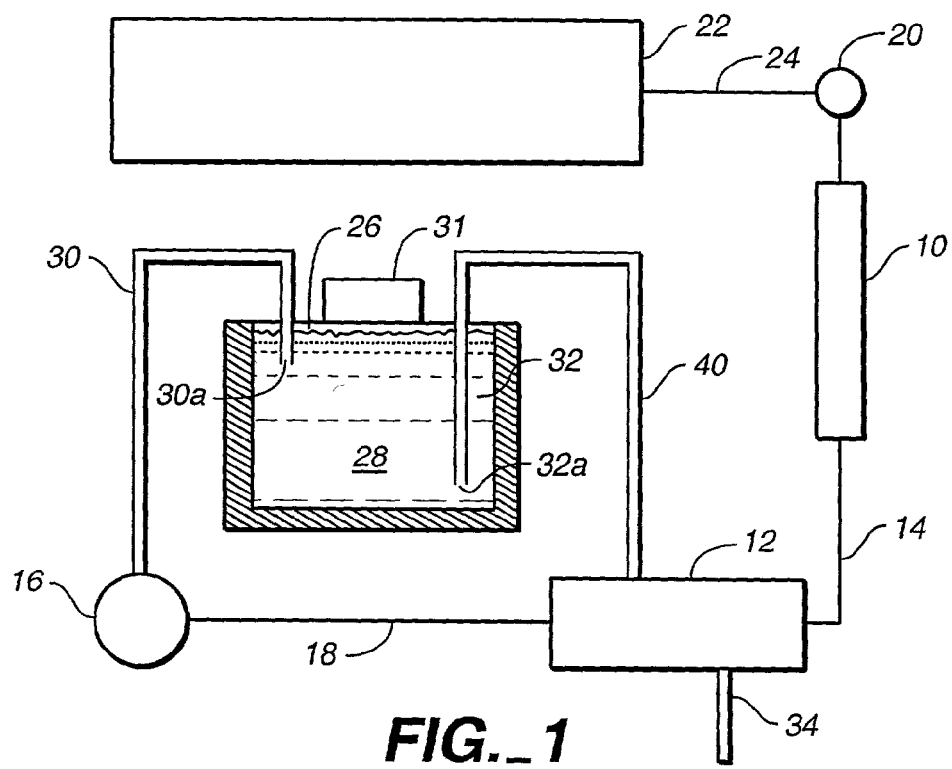
FIG._1
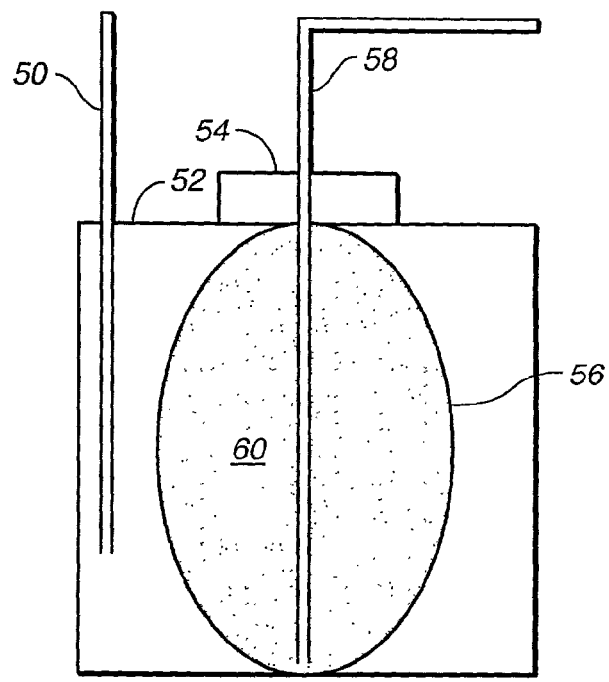
FIG._2

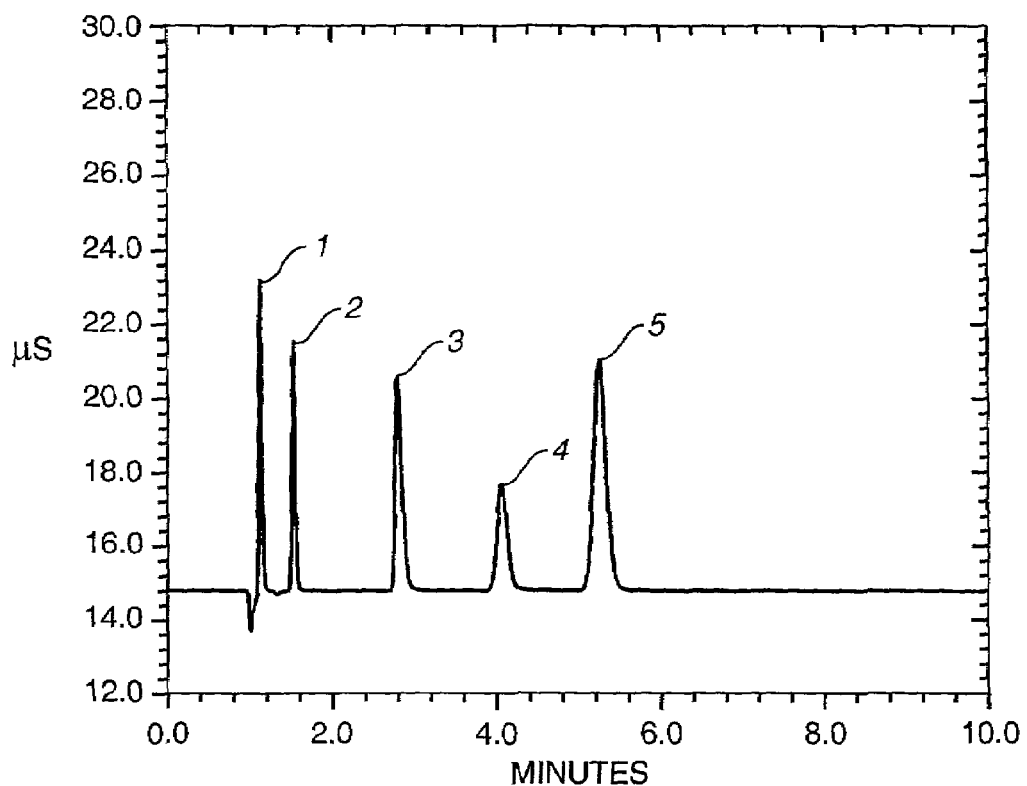
FIG._3
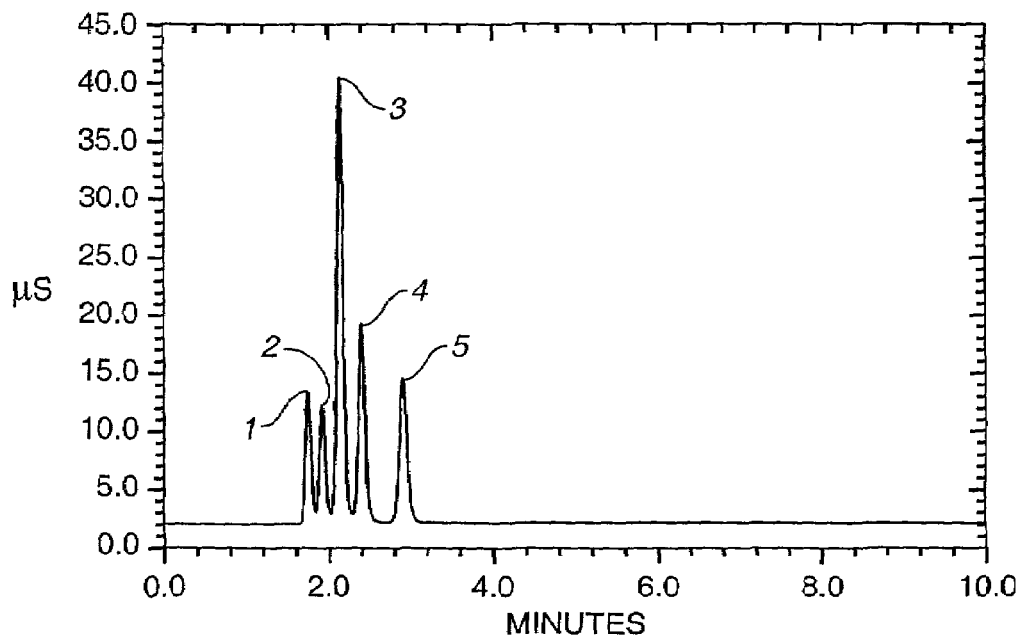
FIG._4

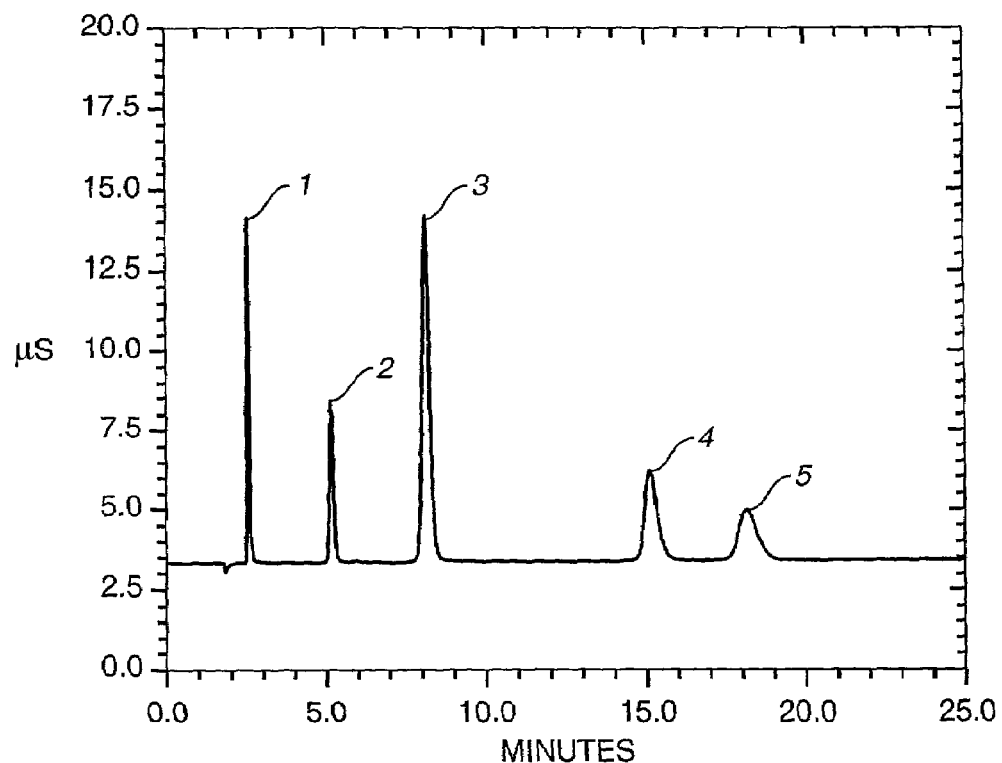
FIG._5
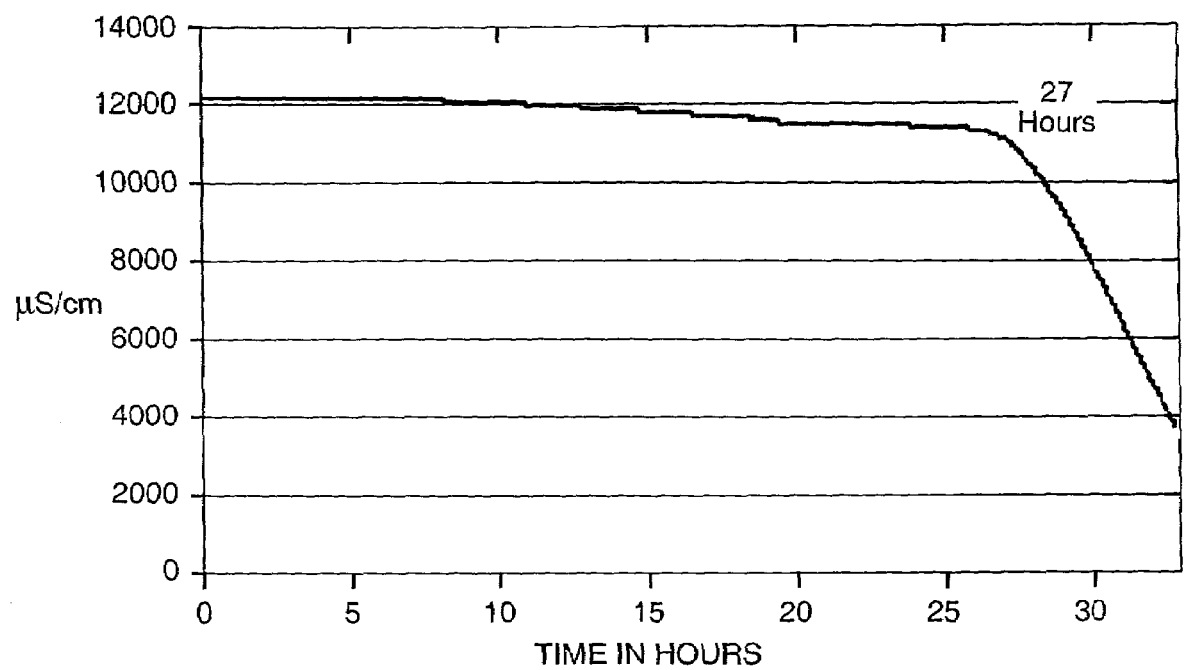
FIG._6

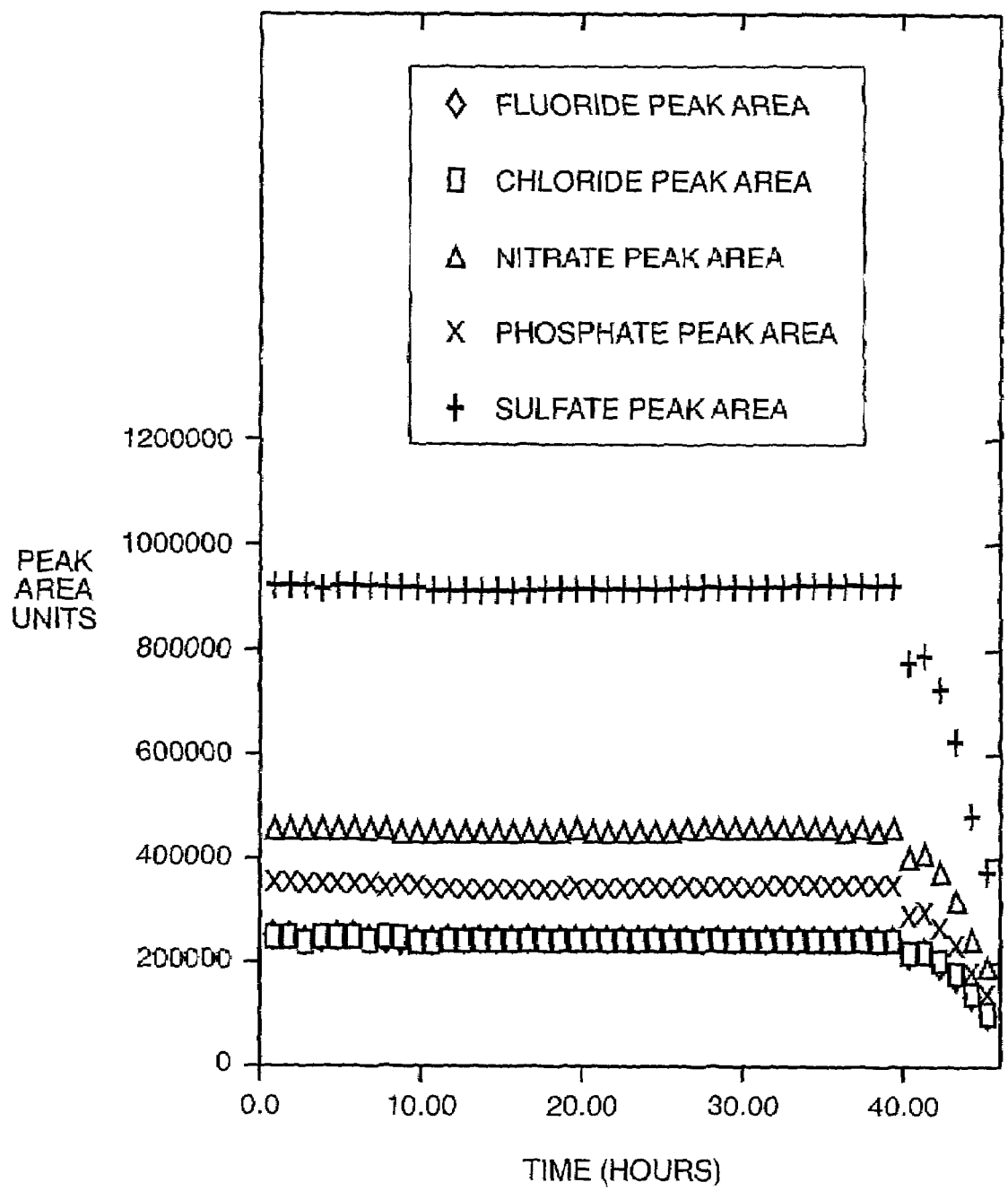
FIG._7

DISPLACEMENT CHEMICAL REGENERATION METHOD AND APPARATUS

This is a divisional of application Ser. No. 09/520,731 filed Mar. 8, 2000 now U.S. Pat. No. 6,436,719.

BACKGROUND OF THE INVENTION

The present invention relates to method and apparatus using suppression of eluents for the analysis of anions or cations in ion chromatography.

Ion chromatography is a known technique for the analysis of ions which typically includes a chromatographic separation stage using an eluent containing an electrolyte, and an eluent suppression stage, followed by detection, typically by an electrical conductivity detector. In the chromatographic separation stage, ions of an injected sample are eluted through a separation column using an electrolyte as the eluent. In the suppression stage, electrical conductivity of the electrolyte is suppressed but not that of the separated ions so that the latter may be determined by a conductivity cell. This technique is described in detail in U.S. Pat. Nos. 3,897,213, 3,920,397, 3,925,019 and 3,926,559.

Suppression or stripping of the electrolyte is described in the above prior art references by an ion exchange resin bed commonly referred to as a packed bed suppressor (PBS). The PBS requires periodic regeneration by flushing with an acid or base solution.

Another approach to regeneration of a PBS is disclosed in U.S. Pat. No. 5,773,115. Ion chromatography is performed by chromatographic separation, chemical suppression in a packed bed and detection. Thereafter, an electrical potential is passed through the packed bed suppressor while flowing an aqueous stream through it to electrolyze water in the stream and thereby create hydronium or hydroxide ions to regenerate the ion exchange resin. The packed bed suppressor has electrodes embedded in the resin for electrochemical regenerant. A second ion exchange resin bed is disclosed with suitable valving to pass liquid streams through the system. In one alternative, a second sample in an eluent stream is chromatographically separated. The eluent and separated second sample flow through a second packed bed suppressor and to a detector. The effluent then flows through the first packed bed suppressor, forming the aqueous liquid stream required for regeneration and an electrical potential is applied for regeneration. The second suppressor may be similarly regenerated by flowing the detector effluent of the first sample through it and applying an electrical potential.

Another form of suppressor known as a "membrane suppressor" is described in U.S. Pat. No. 4,999,098. In this apparatus, the suppressor includes at least one regenerant compartment and one chromatographic effluent compartment separated by an ion exchange membrane sheet. The sheet allows transmembrane passage of ions of the same charge as its exchangeable ions. Ion exchange screens are used in the regenerant and effluent compartments. Flow from the effluent compartment is directed to a detector, such as an electrical conductivity detector, for detecting the resolved ionic species. The screens provide ion exchange sites and serve to provide site to site transfer paths across the effluent flow channel so that suppression capacity is no longer limited by diffusion of ions in the bulk solution to the membrane. A sandwich suppressor is also disclosed including a second membrane sheet opposite to the first membrane sheet and defining a second regenerant compartment. Spaced electrodes are disclosed in communication with both regenerant and chambers along the length of the suppressor. By applying an electrical potential across the electrodes, there is an increase in the suppression capacity of the device. The patent discloses a typical regenerant solution (acid or base) flowing in the regenerant flow channels and supplied from a regenerant delivery source. In a typical anion analysis system, sodium hydroxide is the electrolyte developing reagent and sulfuric acid is the regenerant. The patent also discloses the use of water to replace the regenerant solution in the electrodialytic mode.

Another membrane suppressor is described in U.S. Pat. No. 5,248,426. A direct current power controller generates an electric field across two platinum electrodes to electrolyze water in the regenerant channels. Functionalized ion-exchange screens are present in the regenerant chambers to facilitate electric current passage with permselective ion-exchange membrane defining the chromatography eluent chamber, as in the '098 patent. After detection, the chromatography effluent is recycled through the suppressor to form a flowing sump for electrolyte ion as well as providing the water for the electrolysis generating acid or base for suppression.

A different membrane suppressor is disclosed in EPA Publication WO 99/44054. The suppressor is of the membrane suppressor type even though it includes a flow-through suppressor bed of ion exchange resin. The bed has a liquid sample inlet and an outlet section, a first electrode in an electrode chamber is adjacent to the suppressor inlet section. A barrier separates the suppressor bed from the electrode chamber, preventing significant liquid flow but permitting transport of ions. A second electrode is in electrical communication with said resin bed outlet section. A recycle conduit provides fluid communication between the suppressor outlet and the electrode inlet. In one embodiment of the disclosed method for anion analysis, effluent from a chromatography column is suppressed in cation exchange resin in the suppressor. The effluent from the suppressor flows past a detector and is recycled to the electrode chamber including a cathode. An electrical potential is applied between the cathode and an anode in electrical communication with the suppressor bed. Water is electrolyzed at the anode to generate hydronium ions to cause cations on the cation exchange resin to electromigrate toward the barrier and to be transported across said barrier toward the cathode while water in the cathode chamber is electrolyzed to generate hydroxide ions which combine with the transported cations to form cation hydroxide in the electrode chamber.

SUMMARY OF THE INVENTION

In accordance with the present invention, ionic species in an aqueous liquid sample stream are analyzed by the method of (a) chromatographically separating the ionic species in the presence of an aqueous eluent solution comprising electrolyte to form a chromatographic effluent, (b) suppressing the electrolyte in the chromatography effluent by flowing the same through a suppressor to form a suppressed effluent, (c) detecting the ionic species in the suppressed effluent, and (d) flowing the detected suppressed effluent to a reservoir of regenerant liquid to displace the regenerant liquid and to cause it to flow as a stream out from the reservoir to the suppressor, the suppressed effluent stream being of a different chemical composition than the regenerant liquid. The suppressor can be a membrane suppressor or an ion exchange packing suppressor.

In one embodiment, the regenerant liquid and suppressed effluent have different physical properties so that an interface is formed therebetween. In another embodiment, suppressed effluent is isolated from the regenerant liquid in the reservoir by a movable barrier.

One embodiment of apparatus according to the invention includes (a) a chromatographic separator, (b) a source of an aqueous eluent solution comprising electrolyte in fluid communication with the chromatographic separator, (c) a flow-through ion exchange packing suppressor, including a chromatography effluent flow channel and in fluid communication with the separator outlet, (d) a container including an inlet and an outlet, the container outlet being in fluid communication with the chromatography effluent flow channel, (e) a regenerant liquid reservoir in the container of a different chemical composition than the chromatography effluent, (f) a detector for detecting ionic species in fluid communication with the chromatography effluent flow channel, and (g) a recycle conduit for the flow of effluent from the detector to said container inlet.

In another embodiment of the apparatus, the suppressor is a membrane suppressor comprising a chromatography effluent flow channel separated by an ion exchange membrane from a regenerant flow channel having an inlet and an outlet.

BRIEF DESCRIPTION OF THE DRAWINGS

FIG. 1 is a schematic flow diagram illustrating the present invention using a membrane suppressor.

FIG. 2 is an embodiment of a container containing regenerant liquid useful in the present invention.

FIGS. 3-7 are experimental results illustrating the present invention.

DETAILED DESCRIPTION OF THE PREFERRED EMBODIMENTS

The system of the present invention is useful for determining a large number of ionic species so long as the species to be determined are solely anions or solely cations. A suitable sample includes surface waters, and other liquids such as industrial chemical wastes, body fluids, beverages such as fruits and wines and drinking water. When the term "ionic species" is used herein, it includes species in ionic form and components of molecules which are ionizable under the conditions of the present system.

The present invention relates to suppressed ion chromatography. The purpose of the suppressor is to reduce the conductivity, and hence noise, of the analysis stream background while enhancing the conductivity of the analytes (i.e., increasing the signal/noise ratio), while maintaining chromatographic efficiency. Thus, the following parameters are important to the performance of the suppressor: (1) capacity of the suppressor, measured as eqv/mL of the suppressor resin; (2) the volume of the suppressor; (3) the ratio of the i.d. to the length of the suppressor; and (4) background conductivity measured as $\mu$S/cm for each device.

As used herein, the term "membrane suppressor" includes a suppressor of the general type described in U.S. Pat. Nos. 4,999,098, 5,352,360, and Publication WO 99/44054 incorporated herein by reference. A membrane suppressor includes a chromatography effluent flow channel separated by a liquid impermeable ion exchange membrane from a regenerant flow channel. Effluent from the chromatography separator flows through the chromatography effluent flow channel and from there to the detector. A regenerant liquid flows in the regenerant liquid flow channel on the opposite side of the membrane. The membrane partitioning the flow channels is permselective, i.e., preferentially permeable to ions of one charge only, positive or negative, of the opposite charge to the analyte ions of interest and includes exchangeable ions of that one charge. For example, for anion analysis, the electrolyte in the eluent typically includes a strong cation such as sodium and the membrane is permeable to the sodium ions. During suppression, the sodium ions move across the membrane from the chromatography effluent flow channel to the regenerant flow channel, while hydronium ions move across the membrane from the regenerant flow channel to the chromatography effluent flow channel, thereby suppressing the chromatography effluent prior to detection.

The regenerant liquid can be a chemical regenerant such as an acid or a base for chemical (non-electrolytic) regeneration or can constitute water or effluent from the detector, comprising substantially water, for use as the water source for electrolytic regeneration.

As used herein, the term "ion exchange packing suppressor" refers to a suppressor in which substantially all of the suppression occurs in ion exchange material in the chromatography effluent flow channel of the suppressor and regeneration occurs in a separate operation in the same channel rather than simultaneously using two channels as with the membrane suppressor. The conventional form of ion exchange packing suppressor is a packed bed suppressor (PBR) such as described in U.S. Pat. No. 5,773,615. Alternatively, other forms of ion exchange packing may be employed such as a porous ion exchange monolith through which the chromatography effluent passes, such as disclosed in EPA Publication No. WO 99/11351.

The present invention is based on ion chromatography analysis in which the sample ions are chromatographically separated, the electrolyte of the eluent is suppressed, and the analyte ions are detected. The effluent from the detector flows to a reservoir of regenerant liquid to displace it and cause it to flow from the reservoir to the inlet of a suppressor for regeneration of the suppressor. The use of the recycling detector effluent as a driving force for the regenerant liquid is applicable to any suppressor including a membrane suppressor or an ion exchange packing suppressor such as a packed bed suppressor of the foregoing type.

Referring to FIG. 1, a simplified flow system for performing one embodiment of the present invention is illustrated in which the effluent from the detector and the reservoir of regenerant liquid are not isolated by a physical barrier. Also, the suppressor is of the membrane suppressor type. The system includes a chromatographic separator, typically in the form of a chromatographic column 10 which is packed with a chromatographic separation medium. In one embodiment referred to above, such medium is in the form of ion exchange resin. In another embodiment, the separation medium is a porous hydrophobic chromatographic resin with essentially no permanently attached ion exchange sites such as described in U.S. Pat. No. 4,265,634, incorporated herein by reference.

Arranged in series with column 10 is membrane suppressor 12 serving to suppress the conductivity of the electrolyte of the eluent from column 10 but not the conductivity of the separated ions. Line 14 interconnects the outlet of column 10 with the inlet of the chromatography effluent flow channel of suppressor 12.

The membrane suppressor may be of any conventional type such as described above including a chromatography effluent flow channel separated by an ion exchange membrane from a regenerant liquid flow channel, also termed in this case a detector effluent flow channel in U.S. Pat. No. 5,352,360, incorporated herein by reference. Like that patent, the present invention uses the detector effluent in the regeneration process. However, the present invention includes in addition a reservoir of regenerant liquid which is directed to the regenerant liquid flow channel of suppressor 12.

Referring again to FIG. 1, the effluent from the outlet of the chromatography effluent flow channel of suppressor 12 is directed through line 18 to a detector, preferably a flow-through conductivity cell 16, for detecting the separated ionic species. A suitable sample is supplied through injection valve 20 which is passed through the apparatus in eluent solution from an eluent source or reservoir, not shown, under the influence of conventional pump 22 and passed in line 24 through injection valve 20. After separation, the chromatography effluent solution containing the separated ionic species is directed from the outlet of column 10 through line 14 to the inlet of the chromatography effluent flow channel of suppressor 12 which the electrolyte is suppressed, i.e., converted to a weakly conducting form. In conductivity cell 12 the presence of ionic species produces an electrical signal proportional to the amount of ionic material. Such signal is typically directed from cell 16 to a conductivity meter, not shown, thus permitting detection of the concentration of separated ionic species. As is well known, other types of detectors may also be employed.

The effluent from conductivity cell 16, referred to herein as the detector effluent, is directed to container 26 which contains a reservoir of regenerant liquid 28. The liquid from detector 16 flows through inlet opening 30a of conduit 30, typically in the form of hollow tubing, which projects through a sealed opening in the top wall of container 26. The container is filled with the regenerant liquid at the beginning of the run through an opening in the container which is sealed by the plug or bottle top 31. In the illustrated form of the invention, the regenerant liquid is driven out of container 26 by the pressure of pump 22 and flows through opening 32a of outlet conduit or tubing 32. Tubing 32 terminates at its downstream end in a fitting connecting it with suppressor 12, specifically the inlet port of a regenerant flow channel separated by an ion exchange membrane from a chromatography effluent flow channel as illustrated in this U.S. Pat. No. 5,352,360. The regenerant liquid flows into the inlet of the regenerant liquid flow channel of suppressor 12, through it, and out to waste through line 34 connected to the outlet end of the regenerant liquid flow channel.

The invention is useful in any system in which the detector effluent is of a different chemical composition than the regenerant liquid. For example, the detector effluent may contain components such as organic solvents which could be harmful if recycled to the suppressor. Also, the regenerant liquid, particularly for chemical regeneration, requires acid or base to regenerate the suppressor which would not be present in the detector effluent. The invention also may be used for a suppressor operated in a continuous mode or in a batch (discontinuous) mode.

In certain embodiments, it is preferable for the level at which the detector effluent exits opening 30a and flows into the chamber of container 26 forming the reservoir is higher than the level of outlet 32a in which the regenerant liquid flows out the reservoir. In one embodiment, the regenerant liquid reservoir 28 is present in sufficient volume to provide a significant portion of the liquid required for a complete analytical run cycle. The invention is particularly useful for a chemical regeneration mode as in U.S. Pat. No. 4,999,098 rather than substantially using water as an electrochemical suppression as in U.S. Pat. No. 5,248,426. In the chemical regenerant mode, the regenerant liquid is a chemical regenerant (not only water), such as an aqueous solution of a strong acid (e.g., sulfuric acid) or a base (e.g., sodium hydroxide). For an analysis with sodium carbonate/bicarbonate as the eluent, the suppressed effluent leaving detector 16 typically is carbonic acid. When the carbonic acid is diverted into reservoir 28, it displaces the regenerant (typically a strong acid such as sulfuric acid), thereby providing the driving force to flow the regenerant liquid into the regenerant liquid flow channel of suppressor 12. In this instance, regenerant liquid is denser than the suppressed effluent. Thus, an interface is created between the liquids in a quiescent state, termed the "liquid interface mode." The suppressed effluent floats on top of the regenerant liquid. Here, the inlet 30a can be positioned above the outlet 32a with the interface at an intermediate level. For example, the inlet 30a can be near the top of the liquid regenerant reservoir, or flow into container 26 and the outlet 32a near the bottom. This maximizes utilization of the regenerant from the chamber as the denser liquid is preferentially removed from the container because of the different levels of the inlet and outlet. As long as the interface does not reach outlet 30a, the regenerant liquid is the only liquid flowing from container 26.

Other physical property characteristics which can provide an interface between the suppressor effluent and the regenerant liquid include a polarity differential between the liquids. A difference in viscosity between the suppressor effluent and the regenerant liquid could also provide an interface between the two liquids. Where the two liquids are in direct contact, if it is desired to prevent the suppressed effluent from recycling to the suppressor, the suppressed effluent preferably has a difference in at least one physical property which creates this interface. Other liquid interface modes will be apparent to one of ordinary skill.

The above system can be operated using an analytical eluent pump since the regenerant liquid is driven into the suppressor device under the pressure created by that pump. The regenerant liquid is isolated from the suppressed effluent.

The entire reservoir may be completely filled with regenerant liquid at the beginning of the run. Minimal mixing of the suppressor eluent with the regenerant liquid can be minimized by maintaining the different density liquids in a substantially quiescent state. Most of the regenerant liquid reservoir capacity e.g. greater than 50% to as high as 90% or more may be utilized by this approach.

One or more containers in parallel or series may be used so long as they contain sufficient regenerant liquid for the run cycle. The term "container" refers to one or more containers. Suitable total volumes of either the container and/or the reservoirs can be as small as about 5 ml to 1000 ml to as high as 4000 ml or more.

If the density of the suppressor effluent is greater than the density of the regenerant liquid, the relationship of levels of the inlet and outlet to container 26 may be reversed, that is the inlet for the suppressed effluent may be towards the bottom of the container while the outlet is towards the top of the container. The exact relationship between this difference in elevation may be varied while taking advantage of the principles of the present invention.

While it is advantageous to maintain the foregoing interface for the above embodiment, the present system may also be employed to provide a driving force for a source of regenerant liquid, preferably a chemical regenerant, which can be mixed with the suppressed effluent by a mixer, not shown, in container 26. This is termed the "mixing mode." Here the suppressed effluent slowly dilutes the regenerant liquid to create a continuous dilution device. In this instance, different elevation inlet and outlets for container 26 are not necessary. This system is particularly effective using a concentrated regenerant liquid, e.g., acid or base. In that case, continuous dilution of the regenerant liquid may be adjusted to have minimal impact on the suppression function of the devices. For example, for a two-liter container, dilution by an equal volume of suppressed effluent in the container would form a regenerant liquid at about 50% of the original concentration. If the concentration of the liquid regenerant is at least twice that required for complete suppression, than continuous suppression is possible using the entire volume of the regenerant liquid reservoir. Here, the regenerant liquid is continuously diluted for increased operational life for a single reservoir compared to the case in which the regenerant liquid is completely isolated from the suppressed effluent.

A characteristic, e.g., conductivity or pH, of the regenerant liquid can be monitored by an indicator in the tubing 40 between the container outlet and the regenerant liquid flow channel inlet of suppressor 12. This is useful in either the liquid interface mode or the mixing mode.

In another embodiment using the apparatus of FIG. 1, the suppressor 12 may be an electrochemical suppressor such as of the type described in U.S. Pat. No. 5,352,360, incorporated herein by reference. Here, the regenerant liquid is water. In this electrochemical mode, there can be advantages in isolating the suppressed effluent from the regenerant liquid flowing to the suppressor. There can be certain components such as solvents or contaminants in the suppressed effluent that would interfere with the reaction if directed through the regenerant flow channel of the suppressor. For example, when performing anion analysis, the addition of organic solvents such as methanol to the eluent to impart ion exchange selectivity to the separation is a common practice. The presence of methanol in the effluent limits operation of the prior art membrane suppressor to the external water mode of operation. Recycling the effluent results in oxidation of the solvent to form ionic by-products, which, in turn, increases the background conductivity and noise. The present invention overcomes this limitation by pumping the suppressed effluent containing organic solvent into a regenerant reservoir with water and the water is pumped back into the suppressor for the electrolytic reactions. Thus, the present invention allows use of electroactive solvents for suppressed chromatography.

In all of the above embodiments, eluent displaces the regenerant liquid thereby eliminating the need for an additional pump and control of flow rate of regenerant liquid. Also suppressor exhaustion can be eliminated. Moreover, the use of a pulse-free analytical pump such as a GP50 pump from Dionex Corporation results in lower operational noise and drift.

As set forth above, where it is important to substantially isolate the suppressed effluent from the regenerant liquid supplies to the suppressor, it is preferable to use the liquid interface mode or another embodiment of the invention for the regenerant liquid and suppressed effluent are isolated by a moveable barrier or partition as set out below, termed the "barrier mode."

In one embodiment, the moveable barrier or position can constitute a bag extending across the reservoir and mounted so that the flow of liquid is blocked between the container inlet and container outlet. For example, a flexible liquid impermeable membrane or diaphragm can be mounted as a disk across the cylindrical side wall of container 26 in the form of a cylindrical bottle with the membrane disposed so that the suppressed effluent stays on one side of the barrier and the regenerant liquid is on the other side of the barrier. The barrier is sufficiently flexible and formed so that liquid pressure applied on one side of the barrier by the suppressed effluent flowing into to the container applies pressure to one side of the barrier to force the liquid on the other side of the barrier in the form of regenerant liquid out the container outlet and into the regenerant liquid flow channel. Alternatively, the barrier can be in the form of a piston or disk barrier such as disclosed in U.S. Pat. No. 4,171,757, incorporated herein by reference. The barrier provides the discrimination between the suppressed effluent and the regenerant liquid to drive the regenerant liquid into the regenerant flow channel of the suppressor. Commercially available devices such as under the trade name NowPak container from Now Technologics, Inc. may be employed. Here, the detector effluent is connected to a port in communication with the outside region of a bag and the suppressor inlet is connected to a port in communication with the inside of the bag. In operation, the suppressed effluent urges the regenerant out the bag into the suppressor. Other barrier modes will be apparent to those of ordinary skill.

Referring to FIG. 2, one form of a bag-type of barrier device is illustrated. Detector effluent flows into container 52 in inlet tubing 50 which projects through the top wall of the container. A stopper 54 is removably fitted into an opening in the container top wall to seal the opening. A flexible liquid impermeable bag 56 is mounted to the bottom of stopper 54 and extends into the container with stopper 54 in place. Outlet tubing 58 projects through stopper 54 into the interior of bag 56 and extends to a position near the bottom of the bag and container. The outlet side of tubing 58 is in fluid communication with the suppressor inlet port for regenerant liquid (not shown). At the beginning of the run, regenerant liquid 60 preferably fills most if not substantially all of the interior of bag 56 in its fully expanded state. In operation, liquid from a source described above flows into container 52 through tubing 50 to the exterior of bag 56 to apply pressure against the bag interior to cause it to begin to collapse. This squeezes the regenerant liquid out of the bag, through tubing 58 and into the suppressor inlet port.

The above invention has been described with respect to a membrane suppressor of the chemical regeneration or electrochemical regeneration type. It is also applicable to the use of a suppressor in the form of a flow-through ion exchange packing suppressor as defined above. The most common form of suppressor is the packed bed suppressor which will be used to describe the present system. One such flow system in which the present invention may be employed is illustrated in U.S. Pat. No. 5,633,171 as FIG. 6. There, the suppressors are electrochemically regenerated with the effluent from the on-line suppressor being used as the source of water for electrochemical regeneration of the off-line suppressor. Instead of using electrochemical suppression, the present invention could be performed with the above valving using a chemical regenerant reservoir 28. In this system, the container is disposed between the conductivity detector and the packed bed suppressor with the regenerant liquid reservoir in the container. The liquid from the conductivity cells provides the driving force for the regenerant liquid in the form of an acid or base to regenerate the packed bed suppressor by chemical regeneration. Chemical regeneration is well known as illustrated in U.S. Pat. No. 5,597,734. In fact the present system is similar to the system of that patent with the exception that it eliminates the regenerant liquid pump.

A gas may be mixed with the regenerant liquid stream directed to the suppressor according to the invention as described in application entitled METHOD AND APPARATUS FOR GAS-ASSISTED SUPPRESSED CHROMATOGRAPHY, filed simultaneously herewith (Flehr Docket No. 68965).

In order to illustrate the present invention, the following example exhibits practice are provided.

EXAMPLE 1

A Dionex Corporation DX500 Ion chromatography system was used for anion analysis. The analytical column was AS4a from Dionex Corporation, and the eluent was 1.8 mM $Na_2CO_3$+1.7 mM $NaHCO_3$ at a flow rate of 2 ml/min. The suppressor was a 4-mm ASRS Ultra suppressor. The chemical regenerant was 50 mN $H_2SO_4$ filled in a 4 L container. The regenerant container was plumbed in as shown in the setup in FIG. 1. The above setup resulted in complete suppression of AS4 a eluent and excellent separation of a test mixture of 5 anions was achieved as shown in FIG. 3. The average peak-to-peak noise was 0.48-nS./cm. The analytes were labeled 1) Fluoride 2 mg/L 2) Chloride 3 mg/L 3) Nitrate 10 mg/L 4) Phosphate 15 mg/L and 5) Sulfate 15 mg/L.

EXAMPLE 2

The experimental setup was similar to Example 1, except in this example the chromatographic performance reproducibility was studied. The reproducibility of the separation parameters from this testing (n=19 runs) could be inferred from the following: %RSD peak area=0.3%; %RSD peak ht=0.4%; %RSD Retentiontime=0.24%; %RSD Efficiency=3.2%. The above results demonstrate excellent reproducibility of the above setup.

EXAMPLE 3

A Dionex Corporation DX500 Ion chromatography system was used for anion analysis. The analytical column was AS11 from Dionex Corporation, and the eluent was 21 mM NaOH at a flow rate of 1 min/min. The suppressor was a 4-mm ASRS Ultra suppressor. The chemical regenerant was 50 mN $H_2SO_4$ filled in a bag in a commercially available NowPak Container from Now Technologics. The cell effluent was hooked to a port in communication with the outside region of the bag and the suppressor regenerant flow channel inlet port was connected to a port in communication with the inside region of the bag. In operation, the suppressed cell effluent pushed the regenerant out of the bag into the suppressor regen in port thus enabling suppression to occur. The above setup resulted in complete suppression of the 21 mN sodium hydroxide eluent and excellent separation of a test mixture of 5 anions was achieved as shown in FIG. 4. The average unfiltered peak-to-peak noise was within 0.5 nS/cm. The analytes were labeled 1) Fluoride 2 mg/L 2) Chloride 3 mg/L 3) Sulfate 15 mg/L 4) Nitrate 10 mg/L and 5) Phosphate 15 mg/L.

EXAMPLE 4

A Dionex Corporation DX500 Ion chromatography system was used for anion analysis. The analytical column was AS15 from Dionex Corporation, and the eluent was 38 mM NaOH at a flow rate of 1.2 ml/min. The suppressor was an ASRS Ultra suppressor. The chemical regenerant was 75 mN $H_2SO_4$ filled in a 2 L container. The regenerant container was plumbed in as shown in the setup in FIG. 1. The above setup resulted in complete suppression of the 38-mN sodium hydroxide eluent and excellent separation of a test mixture of 5 anions was achieved as shown in FIG. 5. The analytes were labeled 1) Fluoride 2 mg/L 2) Chloride 3 mg/L 3) Sulfate 15 mg/L 4) Nitrate 10 mg/L and 5) Phosphate 15 mg/L.

EXAMPLE 5

The experimental setup was similar to Example 4 except the column used was AS9HC from Dionex Corporation, and the eluent was 9 mM sodium carbonate. The above setup resulted in complete suppression of the carbonate eluent and excellent separation of a mixture of 5 anions was achieved.

EXAMPLE 6

The experimental setup was similar to Example 4 except the regenerant was 70 mN $H_2SO_4$ and the regenerant conductivity was monitored using a conductivity cell inline and attached prior to entering the suppressor regen-in port. At the eluent flow rate of 1.2 ml/min, a 2-L reservoir with a total capacity of 2.07 L is expected to last for app. 28.75 hours if the entire reservoir is consumed. The conductivity trace as shown in FIG. 6 showed the regenerant conductivity to decrease slowly after greater than 27 hours of continuous operation suggesting a usage rate of over 90% of the total capacity. The above result also suggests that very little mixing was occurring between the cell effluent and the regenerant in the regenerant reservoir.

EXAMPLE 7

A Dionex Corporation DX500 Ion chromatography system was used for anion analysis. The analytical column was AS14 from Dionex Corporation, and the eluent was 3.5 mM sodium carbonate and 1.0 mM sodium bicarbonate eluent at a flow rate of 1.2 ml/min. The suppressor was a 4 mm ASRS Ultra suppressor. The chemical regenerant was 50 mN $H_2SO_4$ filled in a 2 L container. The regenerant container was plumbed in as shown in the setup in FIG. 1 except a magnetic stir bar was placed in the reservoir and the reservoir was placed on a magnetic stir plate. The above setup resulted in complete mixing of the regenerant at any given time. The peak response in area units was plotted against time as shown in FIG. 7. At the eluent flow rate of 1.2 ml/min, a 2 L reservoir is expected to last for approximately 28.75 hours if the entire reservoir is consumed and when the cell effluent is completely isolated from the regenerant. Since the regenerant concentration is chosen to be higher than the eluent concentration, in the continuous dilution mode the regenerant lasts for a longer period of time. The above plot demonstrates this affect and consistent peak areas are observed for over 35 hours of continuous operation.

EXAMPLE 8

A Dionex Corporation DX500 Ion chromatography system was used for cation analysis. The analytical column was CS12A (4×250 mm) from Dionex Corporation, and the eluent was 20 mM MSA at a flow rate of 1 ml/min. The suppressor was a 4 mm CSRS Ultra suppressor. The chemical regenerant was 100 mN+Tetrabutylammoniumhydroxide filled in a 2 L container. The regenerant container was plumbed in as shown in the setup in FIG. 1 except the cell effluent was settled at the bottom of the bottle while the regenerant was sampled from the top and pumped into the regen chamber of the suppressor. The above setup resulted in complete suppression of 20 mN methane sulfonic acid eluent and excellent separation of a test mixture of 6 cations were achieved.

EXAMPLE 9

The experimental setup was similar to Example 8 except the analytical column was CS12a (2×250 mm) and the flow rate was 0.25 ml/min. The suppressor was a 2 mm CSRS Ultra Suppressor. The above setup resulted in complete suppression of 20 mN methane sulfonic acid eluent and excellent separation of a test mixture of 6 cations was achieved.

What is claimed is:

1. Apparatus for analysis of ionic species in an aqueous liquid stream comprising:
    (a) a chromatographic separator including medium for separating said ionic species and having an inlet and an outlet,
    (b) a source of an aqueous eluent solution comprising electrolyte in fluid communication with said chromatographic separator,
    (c) a membrane suppressor comprising a chromatography effluent flow channel separated by an ion exchange membrane from a regenerant flow channel,
    (d) a separate liquid reservoir container independent of said suppressor and including an inlet and an outlet, said container outlet being in fluid communication with said regenerant flow channel, said container having a volume of at least about 5 ml,
    (e) a detector for detecting ionic species in fluid communication with said chromatography effluent flow channel,
    (f) a recycle conduit for the flow of effluent from said detector to said container inlet, and
    (g) a second conduit between said container and suppressor and an indicator disposed in said second conduit for indicating a characteristic of the liquid flowing therebetween.

2. Apparatus for analysis of ionic species in an aqueous liquid stream comprising:
    (a) a chromatographic separator including medium for separating said ionic species and having an inlet and an outlet,
    (b) a source of an aqueous eluent solution comprising electrolyte in fluid communication with said chromatographic separator,
    (c) a membrane suppressor comprising a chromatography effluent flow channel separated by an ion exchange membrane from a regenerant flow channel,
    (d) a separate liquid reservoir container independent of said suppressor and including an inlet and an outlet, said container outlet being in fluid communication with said regenerant flow channel, said container having a volume of at least about 5 ml,
    (e) a detector for detecting ionic species in fluid communication with said chromatography effluent flow channel, a recycle conduit for the flow of effluent from said detector to said container inlet, and
    (g) a moveable piston disposed between said container inlet and outlet moveable in response to liquid pressure.

3. Apparatus for analysis of ionic species in an aqueous liquid stream comprising:
    (a) a chromatographic separator including medium for separating said ionic species and having an inlet and an outlet,
    (b) a source of an aqueous eluent solution comprising electrolyte in fluid communication with said chromatographic separator,
    (c) a membrane suppressor comprising a chromatography effluent flow channel separated by an ion exchange membrane from a regenerant flow channel,
    (d) separate liquid reservoir container independent of said suppressor and including an inlet at a first level in said container and an outlet at a second level in said container different from said first level, said container outlet being in fluid communication with said regenerant flow channel, said container having a volume of at least about 5 ml,
    (e) a detector for detecting ionic species in fluid communication with said chromatography effluent flow channel, and
    (f) a recycle conduit for the flow of effluent from said detector to said container inlet, and
    (g) detector effluent fluid in said recycle conduit, and a reservoir of regenerant liquid in said container of a different chemical composition from said detector effluent.

4. The apparatus of claim 3 in which the regenerant liquid is of a different density than the detector eluent.

* * * * *